United States Patent [19]
Sedmak et al.

[11] Patent Number: 6,103,531
[45] Date of Patent: Aug. 15, 2000

[54] METHODS OF DISRUPTING INTERFERON SIGNAL TRANSDUCTION PATHWAYS

[75] Inventors: Daniel Sedmak, Columbus; Daniel Miller, Hilliard; Brian Rahill; Yingxue Zhang, both of Columbus, all of Ohio

[73] Assignee: Ohio State Research Foundation, Columbus, Ohio

[21] Appl. No.: 09/249,154

[22] Filed: Feb. 12, 1999

Related U.S. Application Data

[60] Provisional application No. 60/074,575, Feb. 13, 1998.
[51] Int. Cl.[7] .............................. C12N 15/63; C12N 5/10
[52] U.S. Cl. ............................................ 435/455; 435/375
[58] Field of Search ................................ 514/44; 435/455

[56] References Cited

PUBLICATIONS

Sedmak et al., Am. J. Pathol. 144: 683–692, 1994, Cytomegalovirus inhibits major histocompatibility class II expression on infected endothelial cells.

Gompels et al., Virology 209: 29–51, 1995, The DNA sequence of human herpesvirus–6: structure, coding content, and genome evolution.

"Viral effects on antigen processing" by Miller, et al., *Current Opinion in Immunology*, Feb. 1999, 11:94–99.

"Human Cytomegalovirus Inhibits IFN–α–stimulated Antiviral and Immunoregulatory Responses by Blocking Multiple Levels of IFN–α Signal Transduction" by Miller, et al. *The Journal of Immunology*, May 15, 1999, 162:6107–6113.

"Human Cytomegalovirus Inhibits Major Histocompatibility Complex Class II Expression by Disruption of the Jak/Stat Pathway" by Miller, et al., *J. Exp. Med.*, vol. 187, No. 5, Mar. 2, 1998, pp. 675–683.

*Primary Examiner*—Robert A. Schwartzman
*Assistant Examiner*—Andrea Ousley
*Attorney, Agent, or Firm*—Calfee, Halter & Griswold LLP

[57] ABSTRACT

A method for reducing levels of JAK 1 and thereby blocking the signal transduction pathways that are employed by IFN-α, IFN-β, and IFN-γ is provided. In one embodiment the method comprises the steps of: providing a cytomegalovirus (CMV) gene product selected from the group consisting of the CMV immediate early gene (IE) products, the CMV early gene (E) products, and combinations thereof; and introducing the CMV gene product or products into cells at levels sufficient to decrease the levels of JAK 1 in the cell. In another embodiment the method comprises the steps of providing a DNA molecule that comprises a CMV IE gene, a CMV E gene, or combinations thereof; introducing the DNA molecule into the cell; and inducing the expression of CMV IE and E genes in the cell, wherein the expression of products encoded by the CMV IE and CMV E genes decreases the levels of JAK 1 in the cell.

15 Claims, No Drawings

METHODS OF DISRUPTING INTERFERON SIGNAL TRANSDUCTION PATHWAYS

This application claims the benefit of U.S. Provisional Application Ser. No. 60/074,575 filing date Feb. 13, 1998.

This invention was made in part with government support under AL38452 awarded by the National Institutes of Health. The U.S. government has certain rights in the invention.

BACKGROUND OF THE INVENTION

Interferons (IFNs) are cytokines with diverse biological functions, including antitumor, immunomodulatory, antiviral and antiparasitic actions. At present, the IFN family includes more than 20 different proteins and is grouped into two types: Type I and Type II. Based on their genetic similarities and differences, the type I IFNs consist primarily of IFN-α an IFN-β. The type II IFNs consist of IFN-γ.

IFNs act by binding to specific cell receptors, which are found on the surface of most cells, and causing the translocation to the nucleus of cytoplasmic transcription factors that enhance or suppress the expression of specific genes. The products of these interferon-stimulated genes are primarily polypeptides that act as mediators of the biological activities associated with the respective IFN.

In the IFN-γ signal transduction (Jak/Stat) pathway, IFN-γ binds to the extracellular heterodimeric receptor subunits IFN-γR1 and IFN-γR2, which are associated intracellularly with Janus kinase 1 (Jak 1) and Janus kinase 2 (Jak 2), respectively. The binding initiates phosphorylation of tyrosine residues in Jak 1, Jak 2, and the cytoplasmic tail of IFN-γR1. Each phosphorylated IFN-γR1 chain becomes a docking site for Stat 1 α, a member of the family of signal transducers and activators of transcription. After docking at the receptor, Stat 1 α is phosphorylated by the Jaks and forms a homodimer known as IFN-γ activation factor (GAF). GAF migrates to the nucleus where it binds the IFN-γ activation sequence (GAS) elements present in the promotors of IFN-γ inducible genes.

High affinity IFN receptors exist on most cells. IFN-α and IFN-β share the same receptor complex. IFN-γ binds to a separate receptor. Nonetheless, IFN-α, IFN-β, and IFN-γ all require the presence of the cytoplasmic protein tyrosine kinase Jak 1 to enhance the expression of specific genes. For example, IFN-γ requires a functional JAK/STAT pathway to upregulate the class II transactivator, CIITA, and thereby induce MHC class II expression.

In certain instances, such as autoimmune diseases, IFN-α, IFN-β, or IFN-γ activation of interferon-stimulation genes can cause a deleterious inflammatory reaction in an individual. Accordingly, it is desirable to have tools and methods for blocking the signal transduction pathways employed by IFNs. It is especially desirable to have tools and methods for reducing levels of JAK 1.

SUMMARY OF THE INVENTION

The present invention provides a method for reducing levels of JAK 1 and thereby blocking the signal transduction pathways that are employed by IFN-α, IFN-β, and IFN-γ . In one embodiment the method comprises the steps of: providing at least one cytomegalovirus (CMV) gene product selected from the group consisting of the CMV immediate early gene (IE) products, the CMV early gene (E) products, and combinations thereof; and introducing the CMV gene product or products into cells at levels sufficient to decrease the levels of JAK 1 in the cell. In another embodiment the method comprises the steps of providing a DNA molecule that comprises at least one CMV IE gene, or at least one CMV E gene, a plurality of CMV IE genes, a plurality of CMV E genes, or combinations thereof; introducing the DNA molecule into the cell; and inducing the expression of CMV IE and E genes in the cell, wherein the expression of products encoded by the CMV IE and CMV E genes decreases the levels of JAK 1 in the cell.

In accordance with the present invention it has been determined that expression of a CMV IE gene, a CMV E gene, or combinations thereof in cells lowers the level of JAK 1 in the cytoplasm of such cells and, thus, blocks the signal transduction pathways that utilize JAK1. It has also been determined that expression of CMV IE and CMV E genes does not lower levels of Jak 1 mRNA. Accordingly, it is believed that the CMV gene product acts by increasing the degradation of Jak 1 protein.

The present method is useful for blocking the activation of interferon stimulated genes such as for example, the gene that encodes CIITA. The present method is also a useful research tool for characterizing the JAK1 pathway. As such, the present method is useful for producing cells which can be used to identify the growth factors, cytokines, and chemokines which require JAK1 in order to activate genes. The present method is also useful for identifying the signaling pathways that require or employ JAK1 and/or for identifying the genes that are activated by the JAK1 kinase pathway. The present method is also useful for studying the regulation of JAK 1 expression and the interaction of JAK 1 with other constituents of signal transduction pathways.

DETAILED DESCRIPTION OF THE INVENTION

CMV IE and E Genes

The CMV immediate early (IE) genes and the CMV early (E) genes encode a set of CMV gene products that are expressed prior to viral DNA replication. CMV IE gene products and CMV E gene products include a variety of enzymes involved in viral DNA synthesis, nonstructural proteins, and some structural proteins and glycoproteins. The known CMV IE genes are located within four transcription units, designated TRS1, US3, UL122–123, and UL36–38. As used herein the term "transcription unit" refers to a segment of the CMV genome that contains one or more genes. The known CMV IE genes encode 12 known proteins: UL36, UL37x1, UL37, UL119–117, IRS1, TRS1, IE72, IE86, IE55, and 3 splice variants of US3. The known CMV E genes are located within the transcription units designated as UL112–113, UL4, UL44, UL54, UL57, UL69, UL70, UL84, UL102, and UL105.

The present invention provides a method which employs CMV IE and/or CMV E genes or gene products to block the signal transduction pathways which utilize JAK1. In one embodiment the method comprises introducing a CMV IE protein, a CMV E protein, or combinations thereof into the cytoplasm of the cell. The protein is introduced in an amount sufficient to reduce the levels of JAK1 in the cell, preferably to levels that are undetectable using western blot analysis. Preferably, the method comprises introducing a CMV protein selected from the group consisting of UL36, UL37x1, UL37, UL119–117 IRS1, TRS1, IE72, IE55, and combinations thereof into the cell.

In another embodiment, the method comprises the steps of introducing a DNA comprising a sequence which encodes a CMV IE gene, a CMV E gene, or a combinations thereof into the cell; and then inducing the expression of these CMV genes in the cell. Preferably the construct comprises a gene sequence located in a transcription unit selected from the group consisting of TRS1, US3, UL122–123, UL36–38, UL112–113, UL4, UL44, UL54, UL57, UL69, UL70, UL84, UL102, UL105, and combinations thereof. Preferably, the DNA is introduced into the cell using a viral vector.

A. Obtaining CMV IE and E Proteins

CMV IE and CMV E proteins are obtained by synthetically producing such proteins using conventional peptide synthesizers. Alternatively, CMV IE proteins and CMV E proteins are produced using cell-free translation systems and RNA molecules derived from DNA constructs that encode the protein. CMV IE protein and CMV E proteins are also made by transfecting host cells with expression vectors that comprise a DNA sequence which encode CMV IE or CMV E proteins, and then inducing expression of the polypeptide in the host cells.

Suitable expression vectors include for example chromosomal, nonchromosomal and synthetic DNA sequences, e.g., derivatives of SV40; bacterial plasmids; phage DNA's; yeast plasmids; vectors derived from combinations of plasmids and phage DNAs, viral DNA such as vaccinia, adenovirus, fowl pox virus, and pseudorabies. The DNA sequence is introduced into the expression vector by conventional procedures.

The polynucleotide sequence encoding the CMV IE and/or E proteins is incorporated into the vector in appropriate phase with translation initiation and termination sequences, and preferably, a leader sequence capable of directing secretion of the translated protein into the periplasmic space or extracellular medium. Optionally, the sequence can encode a fusion CMV IE or E protein which includes an N-terminal or C-terminal peptide or tag that stabilizes or simplifies purification of the expressed recombinant product. Representative examples of such tags include sequences which encode a series of histidine residues, the Herpes simplex glycoprotein D, or glutathione S-transferase.

The expression vectors are expressed in suitable host cells, such as for example, mammalian cells, yeast, bacteria, or other cells under the control of appropriate promoters. Following transformation of the suitable host strain and growth of the host strain to an appropriate cell density, the cells are typically harvested by centrifugation, disrupted by physical or chemical means, and the resulting crude extract retained for further purification of CMV IE and/or CMV E proteins.

The recombinant CMV protein that is expressed in a host cell culture is usually isolated by initial extraction from cell pellets or from cell culture medium, followed by salting-out, and one or more chromatography steps, including aqueous ion exchange chromatography, size exclusion chromatography steps, and high performance liquid chromatography (HPLC). Optionally, purification is accomplished using antibodies that bind to the respective CMV protein.

B. Administering the Protein

CMV proteins are introduced into the cytoplasm of individual target cells by standard techniques such as, for example, microinjection. Alternatively, the CMV IE protein, the CMV E protein or combinations thereof, are introduced into the cytoplasm of a larger number of cells using protein delivery systems, such as, for examples, liposomes. Such delivery systems are used both in vitro and in vivo to introduce proteins into the cytoplasm of target cells.

Standard techniques are also employed to determining the amount of the CMV IE and/or the CMV E protein needed to reduce the amount of the signal transduction protein JAK1 to desired levels. For example, the desired amount of protein can be determined by introducing different amounts of the CMV IE and or the CMV E protein into the target cell; lysing the cells after a period of from about 24 to 48 hours; and then assaying for the absence of detectable levels of JAK1 in the cell lysate using standard western analysis.

II.

Administering a DNA Comprising a Sequence that Encodes a CMV IE Protein a CMV E Protein or Combinations Thereof Into a Cell Recombinant constructs comprising a sequence which encodes CMV IE and/or E proteins are introduced into cells using standard techniques. Suitable constructs are, for example, a vector, such as a plasmid, phagemid, or preferably a viral vector, into which a sequence which encodes CMV IE and/or E proteins has been inserted.

Electroporation or calcium-chloride mediated transfection is preferably used to introduce the constructs into cells in vitro. Preferably, viral vectors such as for example retroviral vectors, adenoviral vectors, or parvoviral vectors, preferably, the recombinant adeno-associated virus vector, are used to introduce the DNA into cells in vivo.

In the vector, the DNA sequence which encodes CMV IE and/or the CMV E protein is operatively linked to an expression control sequence, i.e., a promoter, which directs mRNA synthesis. The promoter may be an inducible promoter or a constitutive promoter. Representative examples of such promoters, include the LTR or SV40 promoter, or any other promoter which promotes expression in eukaryotic cells, preferably mammalian cells, more preferably lymphocytes. The promoter may also be the potent CMV immediate/early promoter. The expression vector also contains a ribosome binding site for translation initiation and a transcription terminator. Optionally, the recombinant expression vector contains a selectable marker, such as for example, the ampicillin resistance gene of *E. Coli* to permit selection of transformed cells, i.e. cells that are expressing the heterologous DNA sequences. A method of preparing a recombinant adeno-associated virus vector containing a heterologous DNA sequence is described in an article by Peng. L. et. al entitled "Construction of recombinant adeno-associated virus vector containing the rat preproinsulin II gene." and published in J. Surg. Res. 69:193–198 (1997), which is specifically incorporated herein by reference.

The viral vector is then introduced into the animal by intravenous, intraperitoneal, or intramuscular injection. Thereafter, the CMV IE protein and/or the CMV E protein is expressed in the cell. Depending on the type of promoter used, the expression is induced or occurs constitutively.

Another method for introducing DNA which contains the sequences encoding CMV IE gene products and CMV E gene products into a cell involves infection with replicating CMV or with non-replicating CMV. In those instances where cells are infected with replicating CMV, i.e., replicative-competent CMV, expression of CMV late (L) gene products is blocked by inhibiting production of CMV DNA polymerase in the infected cell or by inhibiting the enzymatic activity of CMV DNA polymerase in the infected cell. In addition to blocking expression of CMV L gene products, such treatment blocks replication of CMV.

Cells are infected with replicating CMV, preferably at a multiplicity (MOI) of from about 0.1 to about 7. Expression of CMV L gene products is blocked by introducing compounds which inhibit CMV DNA polymerase activity such as, for example, phosphonoformic acid (PFA,) and ganciclovir (GCV). Alternatively, the cells are treated with antisense oligodeoxynucleotides (ODN) to the CMV DNA polymerase prior to infection. The ODN function by binding to sense mRNA molecules and preventing translation. ODN sequences, preferably 18 mers, are selected from the HCMV DNA polymerase cDNA sequence. To optimize suppression of mRNA translation, it is preferred that the 5' region of the mRNA overlapping the AUG initiation codon be used as an antisense target. Preferably, each ODN is synthesized on a DNA synthesizer using phosphoramidite chmistry and derivitized to the phosphorothioates using the Beaucage reagent as a sulfur donor. Preferably, the cells are treated with 0.1 to 20 μM ODN in the presence of cationic liposomes. Quantitative Western blot analysis is used to assess the efficacy of the antisense oligonucleotides in preventing CMV DNA polymerase expression.

Production of CMV L gene products may also be blocked by infecting cells with a mutant non-replicating CMV, which comprises a genome that lacks a functional DNA polymerase.

Measuring the Levels of JAK 1 in the Cells

Preferably, the levels of JAK 1 in the cells are measured using an immunoassay. Suitable immunoassays include, by way of example, radioimmunoassays, both solid and liquid phase, fluorescence-linked assays or enzyme-linked immunosorbent assays.

The following examples are for purposes of illustration only and are not intended to limit the scope of the claims which are appended hereto.

EXAMPLE 1

Human embryonic lung fibroblasts (MRC-5), passages 22 to 35, were cultured in Eagle's minimum essential medium supplemented with 10% fetal bovine serum (Gibco) at 37° C. in a 5% $CO_2$ incubator. Towne HCMV at an MOI of 3 was incubated with the fibroblasts for 2 hours at 37° C. and free virus washed off (time zero). To inhibit expression of HCMV L gene products and to allow expression of the CMV E and CMV IE gene products, cells were infected with Towne HCMV in the presence of 2 mM phosphonoformic acid (PFA,) obtained from Sigma and 0.6 mM Ganciclovir (GCV) from Cytovene.

At 72 hours post-infection, untreated CMV infected fibroblasts and CMV-infected fibroblasts treated with PFA/GCV were stimulated with 200 U/ml IFN-γ for 30 minutes, nuclear extracts recovered, and EMSA was performed to monitor the formation of GAF. The levels of the CMV L gene product glycoprotein B and the CMV IE gene product IE1 were also determined.

The results indicated that HCMV infection in the presence of PFA/GCV inhibited expression of the CMV L gene product glycoprotein B (gB), without inhibiting expression of the CMV IE gene product IE1. These results also indicate that a method which involves expressing a CMV E gene product, a CMV IE gene product, or combinations thereof in a cell inhibits IFN-γ stimulated signal transduction in such cell.

What is claimed is:

1. A method for decreasing levels of Janus kinase I (JAK 1) in a cell comprising:
   (a) providing an isolated cytomegalovirus (CMV) gene product selected from the group consisting of a cytomegalovirus early (CMV E) gene product, a cytomegalovirus immediate early (CMV IE) gene product, and combinations thereof; and
   (b) introducing said isolated gene product into said cell in an amount sufficient to reduce levels of the JAK 1 in said cell.

2. The method of claim 1, wherein the CMV gene product is a CMV E gene product.

3. The method of claim 1, wherein the CMV gene product is a CMV IE gene product.

4. The method of claim 1, wherein the CMV gene product is selected from the group consisting of UL36, UL37x1, UL37, UL119–117 IRS1, TRS1, IE72, IE55, and combinations thereof.

5. The method of claim 1, wherein the CMV gene product is encoded by a sequence contained with a transcription unit selected from the group consisting of TRS1, UL122–123, UL36–38, and combinations thereof.

6. The method of claim 1 wherein the CMV gene product is encoded by a sequence contained within a transcription unit selected from the group consisting of UL112–113 UL4, UL44, UL54, UL57, UL69, UL70, UL84, UL102, UL105, and combinations thereof.

7. The method of claim 1 further comprising the step of measuring levels of JAK1 in the cell.

8. A method for decreasing levels of JAK 1 in a cell comprising:
   (a) providing a construct comprising a CMV gene selected from the group consisting of a CMV E gene, a CMV IE gene, and combinations thereof;
   (b) introducing said construct into said cell; and
   (c) expressing the gene product of said CMV gene, wherein said gene product is expressed in an amount sufficient to reduce levels of the JAK 1 in said cell.

9. The method of claim 8, wherein said CMV gene is a CMV E gene.

10. The method of claim 8, wherein said CMV is a CMV IE gene.

11. The method of claim 8 wherein said CMV gene is located in a CMV transcription unit selected from the group consisting of TRS1, US3, UL122–123, UL36–38 and combinations thereof.

12. The method of claim 8 wherein said CMV gene is located in a CMV transcription unit selected from the group consisting of UL112–113, UL4, UL44, UL54, UL57, UL69, UL70, UL84, UL102, UL105, and combinations thereof.

13. A method for decreasing levels of Janus kinase 1 in a cell comprising:
   (a) infecting said cell with a replicative-competent CMV; and
   (b) treating said cell with an inhibitor of CMV DNA polymerase to prevent replication of said CMV and to block expression of CMV L gene products, such that levels of JAK 1 are reduced.

14. The method of claim 8 further comprising the step of measuring levels of JAK1 in the cell .

15. The method of claim 1 wherein the isolated CMV gene product is a protein.

* * * * *